United States Patent [19]

Mitnick

[11] Patent Number: 5,030,093

[45] Date of Patent: Jul. 9, 1991

[54] METHOD AND APPARATUS FOR DENTAL RESTORATIVE MATERIAL

[75] Inventor: Neal I. Mitnick, Brooklyn, N.Y.

[73] Assignee: Aaron Teitelbaum, Brooklyn, N.Y.; a part interest

[21] Appl. No.: 205,222

[22] Filed: Jun. 10, 1988

[51] Int. Cl.⁵ .............................................. A61C 3/08
[52] U.S. Cl. ................................ 433/164; 433/215; 433/229
[58] Field of Search ............... 433/164, 90, 215, 229

[56] References Cited

U.S. PATENT DOCUMENTS

| | | | |
|---|---|---|---|
| 2,186,143 | 3/1939 | Neugass | 128/634 |
| 3,735,492 | 5/1973 | Karter et al. | 2/60 |
| 4,445,858 | 5/1984 | Johnson | 433/229 |
| 4,449,928 | 5/1984 | von Weissenfluh | 433/229 |
| 4,553,936 | 11/1985 | Wang | 433/229 |
| 4,615,679 | 10/1986 | Wyatt | 433/229 |
| 4,661,070 | 4/1987 | Friedman | 433/203.1 |
| 4,666,405 | 5/1987 | Ericson | 433/215 |
| 4,666,406 | 5/1987 | Kanca, III | 433/229 |
| 4,673,353 | 6/1987 | Nevin | 433/229 |
| 4,726,770 | 2/1988 | Kurer | 433/215 |
| 4,764,118 | 8/1988 | Touati et al. | 433/229 |

OTHER PUBLICATIONS

Parkell Products Update, Products & Techniques for the Dentist, Winter 1987/88 Issue, Advertisement for "Transparent Cure-Through Double Ended Instruments".

Primary Examiner—John J. Wilson
Attorney, Agent, or Firm—Rosen, Dainow & Jacobs

[57] ABSTRACT

A method and apparatus for placing, compacting and shaping a light-activated dental restorative material in a cavity preparation or between adjacent teeth and for polymerizing said restorative material in said cavity preparation or between said teeth to produce a restorative are disclosed. A mirror/oral illuminator and a combination mirror and fiber optic probe are also disclosed.

27 Claims, 5 Drawing Sheets

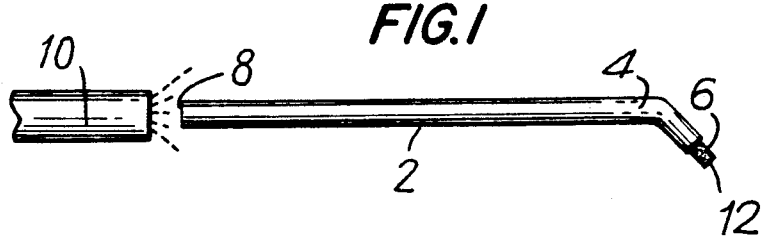
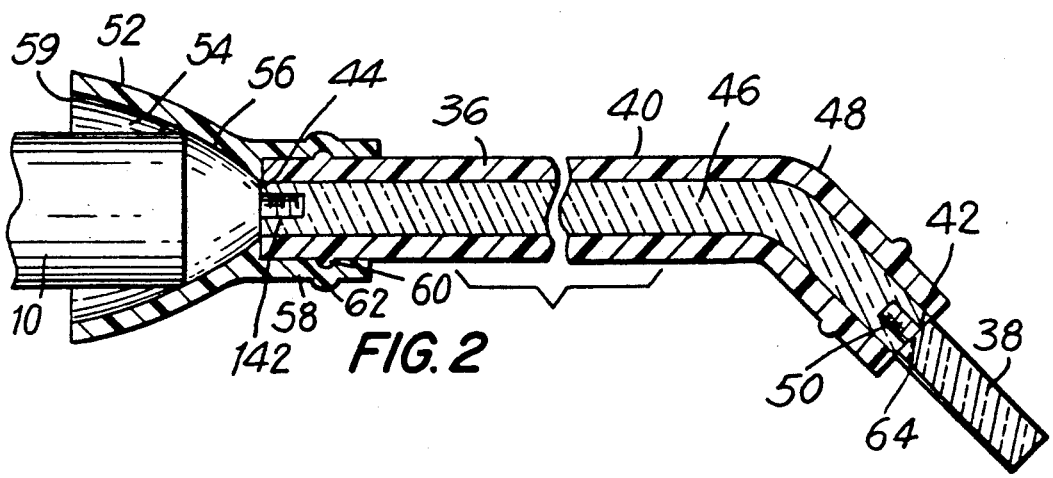
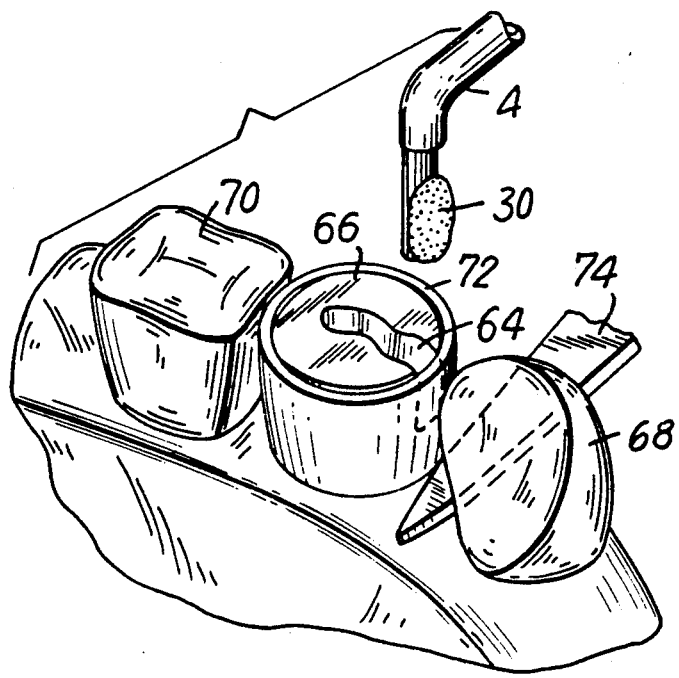

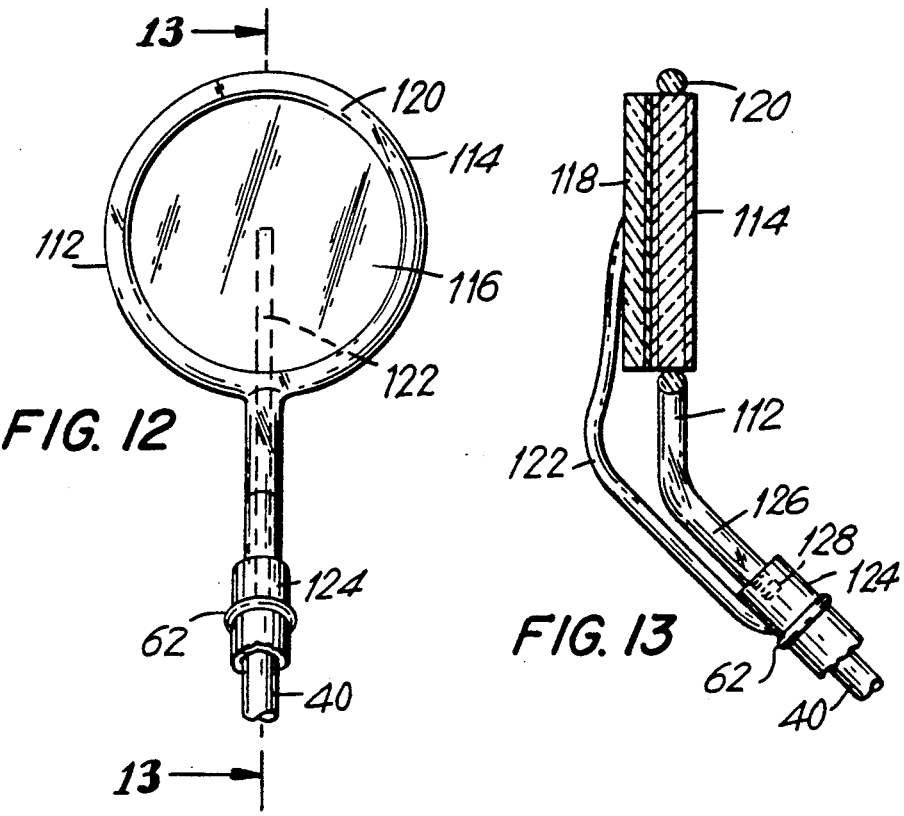
FIG. 12
FIG. 13
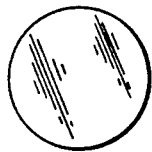
FIG. 14
FIG. 15
FIG. 16
FIG. 17
FIG. 18
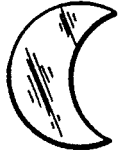
FIG. 19
FIG. 20
FIG. 21
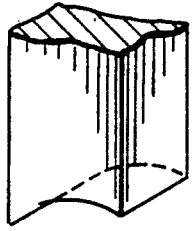
FIG. 23
FIG. 22

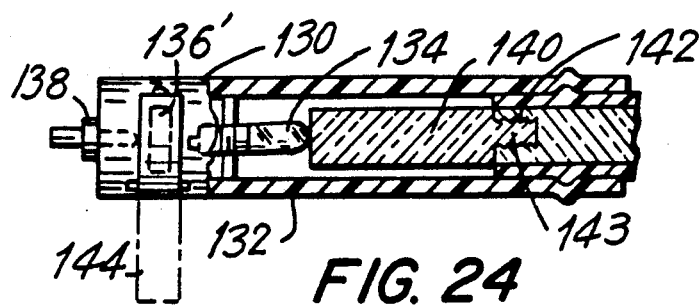
FIG. 24
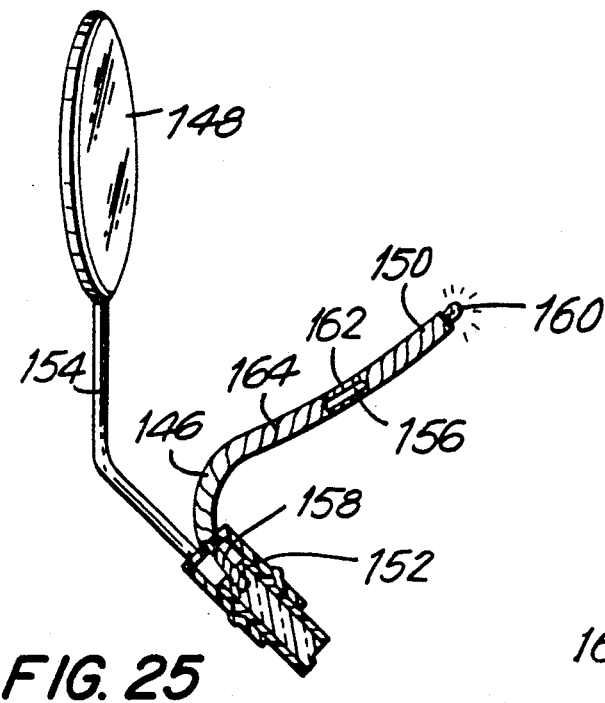
FIG. 25
FIG. 26
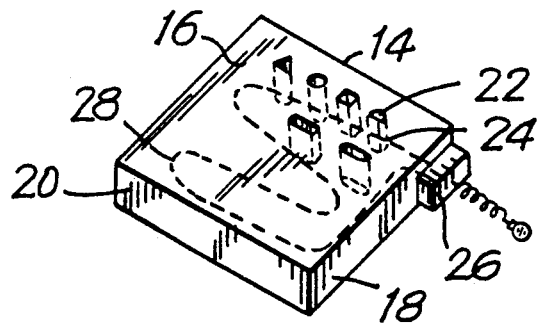
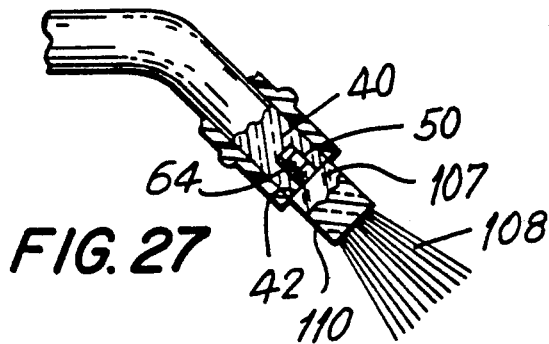
FIG. 27

METHOD AND APPARATUS FOR DENTAL RESTORATIVE MATERIAL

BACKGROUND OF THE INVENTION

1. Field of the Invention

This invention relates generally to dentistry and in particular to a method and an apparatus for placing, compacting and shaping a light-activated dental restorative material in a cavity preparation or between adjacent teeth and for polymerizing said restorative material in said cavity preparation or between said teeth to produce a restoration.

2. Description of the Prior Art

Increasingly, dentists have been using light-curable dental composites as restorative materials. The composite is generally applied to the tooth using a conventional placement instrument or a plastic filling instrument. The composite material is compacted using a condenser and contoured to the shape of the cavity preparation using a carver or bur. When light is shined on the composite for a predetermined time, the composite is polymerized and bonds to the tooth.

Typically, light is transmitted from a light source by a fiber optic cable and a hand-held light wand. The light intensity on the surface of the restoration depends on the light source and the distance of the light source from the restoration. To insure depth of cure, the light should not be held too far away from the restoration. This is difficult to assess when using a hand-held light wand. If the light wand is held too close to the restoration, only a small area is illuminated, leaving marginal areas inadequately cured.

A transparent, cure-through, double-ended instrument is disclosed in Parkell Products Update catalog, Winter 1987/88 issue. The Parkell instrument is a double ended instrument made of light conducting polycarbonate and is autoclavable or cold sterilizable. The working ends of the instrument are polished, whereas the handle comprising the middle portion of the instrument is matted or abraded. In using this double-ended instrument, curing light is applied and transmitted from a direction perpendicular to the handle. As is well known, a polished surface reflects light internally whereas a matted surface diffracts or emits light. Thus, a significant amount of light is emitted from the matted surface of the handle of the Parkell instrument and lost before it can be transmitted to the working ends. The instrument is inefficient and as a practical matter requires increased curing light exposure time to insure depth of cure.

U.S. Pat. No. 4,673,353 to Nevin discloses an apparatus for exposing a light-curable dental composition to a curing light to harden the composition while the composition is applied to teeth so that the exposure of a dentist's eyes to such light is minimized. Nevin's apparatus has an opaque receptacle which is open at its top and bottom; dental composition is picked up and discharged through the bottom opening. An elongated plunger having a clear plastic core and an opaque surface coating has a working end which extends through the top opening of the receptacle and an opposite end connected to a source of curing light. In Nevin's invention, the dental composition is exposed to curing light transmitted from the working end of the plunger while the filling material is held within the receptacle and while the working end of the plunger is forcing the filling material out of the receptacle onto a tooth. Nevin further discloses modifying the apparatus by in part eliminating the opaque receptacle and shaping the working end of the plunger so that the plunger can be used as a tool for shaping light curable composition. However, to protect the user's eyes, Nevin retains the opaque coating on the side surfaces of the plunger between its ends. This limits the usefulness of the apparatus as curing light is emitted only from the tip of the working end of the apparatus and not from its sides.

U.S. Pat. No. 4,666,406 to Kanca, III, discloses an attachment device for a fiber optic wand comprising a rod shaped or needle like fiber optic tip or end cap. In practice, the fiber optic tip is placed in close proximity to composite resin in a cavity preparation and the light source is activated so as to expose the composite resin to a substantially proximate curing light source. The device cannot be used to place, compact and shape dental restorative material in a cavity preparation; neither can it be held against the shaped and compacted restorative material to maintain the desired shape of the restoration while curing light is delivered to the restorative material.

SUMMARY AND OBJECTS OF THE INVENTION

This invention relates, in part, to a method and apparatus for placing, compacting and shaping a light activated dental restorative material in a cavity preparation, between adjacent teeth or onto a pulpal wall and for polymerizing said restorative material in said preparation, between said teeth, or in said pulpal wall by exposing the material to curing light emitted from the tip and all sides of the working end of the apparatus, so as to harden the restorative material and bond it to the tooth, thereby producing a restoration. The method and apparatus of this invention maximizes illuminating efficiency so as insure depth of cure. Exposure time required for polymerization of the restorative material is also kept to a minimum. As the instrument is left in place during curing, there is no pull-back of the restorative material caused when the instrument is removed, and thus, no shrinking or marring of the restoration.

It should be understood that while the present invention finds its most important application in dentistry, it is not limited in scope to dental applications. It is contemplated that the method and apparatus of this invention may be used to place, compact and shape any light-curable resin restorative material against any hard biological tissue or surface, and to polymerize said resin against said tissue or surface to produce a restoration. Among the hard biological tissues or surfaces contemplated are tooth, enamel, dentin, bone, cartilage, and connective tissue. What is meant by a light curable resin is any organic substance in the presence of a solvent and a light cure initiator, such as camphoroquinone, which can be used as a restorative material.

The method involves providing a disposable, polished, rigid, fiber optic handle member having an exposed working end of reduced diameter and an opposite butt end for receiving light. The dentist holds the handle member and uses the working end to place dental restorative material in a cavity preparation, between adjacent teeth or onto a pulpal wall, and to compact and shape the restorative material to the desired contour and depth. While holding the working end against the shaped and compacted restorative material in the preparation or between the teeth or against the pulpal wall to maintain the desired shape of the restoration the dentist approximates a source of curing light to the butt end of the handle member. The light source is activated and curing light is transmitted substantially undiffracted through the length of the polished handle member to diffuse out from the tip and all sides of the matted working end. The light impinges upon the restorative material until the latter is polymerized and bonds to the tooth. It should be noted that the restorative material may conform, adhere or adapt to the preparation or other hard biological tissue or surface to be restored by means of mechanical retention, even in the absence of chemical bonding.

The apparatus utilized in part comprises a rigid handle member having a proximal and a distal end. The handle member comprises a fiber optic core enclosed on its side surfaces, between its ends, within an opaque housing which prevents light, transmitted from one end of the apparatus to the other, from being substantially visible from the side surfaces of the handle member. The proximal end of the handle member is connected to a removable, replaceable and optionally disposable working end member, and the distal end of the handle member is connected to a source of curing light.

Removable and replaceable interchangeable working ends may be rapidly attached to or detached from the handle member of the apparatus during the course of performance of dental work. In one embodiment, the working end member comprises a fiber optic member having a configuration approximating that of a surface or surfaces of a cavity preparation or of a tooth to be restored. The working end member is used to place, compact and shape light activated dental restorative material in the preparation or between the teeth and to polymerize the material in the preparation or between the teeth by exposing the material to curing light emitted from the tip and all sides of the working end member. In another embodiment, the working end of the apparatus may comprise a fiber optic member having a configuration approximating that of the pulp of a tooth for applying and polymerizing light curable calcium hydroxide in a direct pulp cap, pulpotomy or indirect pulp cap procedure in a tooth.

In a further embodiment, the working end member of the apparatus has a configuration corresponding to the ideal crown preparation of the tooth to be restored for core build-up of a tooth in a post and core restoration, for acceptance of a cast crown. In another embodiment, the working end member of the apparatus has a configuration corresponding to the ideal tooth preparation of the tooth to be restored for complete or partial coronal build-up of the tooth. In yet another embodiment, the working end member of the apparatus may comprise a brush for painting and polymerizing light curable dental restorative material, including bonding agent, on a tooth.

In other and further embodiments of this invention, the working end of the apparatus of this invention may comprise a mirror/oral illuminator or a mirror/fiber optic probe. The light source used in connection with these embodiments may be either a hand-held light wand or a portable light source.

Accordingly, it is an object of this invention to provide a method for placing, compacting and shaping a light activated dental restorative material in a cavity preparation, between adjacent teeth or against a pulpal wall, and for polymerizing said restorative material in said preparation, between said teeth or against said pulpal wall.

It is another object of this invention to provide a method and an apparatus for placing, compacting and shaping a light activated composite resin against any hard biological tissue or surface, and to polymerize said resin against said tissue or surface to produce a restoration.

It is a further object of this invention to provide a method and an apparatus for polymerizing composite restorative material whereby curing is effected without causing shrinking, marring or pull-back of the restoration.

Another object of this invention is to provide a light conducting apparatus for carrying out the method of the invention which is simple in design, easy to manufacture, and efficient and reliable in operation.

A further object of this invention is to provide a method for placing, compacting, shaping and polymerizing dental restorative material in a cavity preparation, between adjacent teeth or against a pulpal wall, whereby the working end of the apparatus may be heated or cut by a handpiece or other instrument, and the tip and sides of the working end shaped to a desired configuration approximating that of a surface or surfaces of the cavity preparation or the tooth to be restored.

A further object of this invention is to provide an apparatus having removable and replaceable interchangeable working ends which may be rapidly attached to or detached from the apparatus during the course of performance of dentistry.

A further object of this invention is to provide an apparatus for applying and polymerizing dental restorative material for complete or partial coronal build-up of a tooth.

A further object of this invention is to provide an apparatus for applying and polymerizing dental restorative material for core build-up in a post and core restoration in a tooth for acceptance of a cast crown restoration.

A further object of this invention is to provide a light conducting mirror/oral illuminator for oral use.

A further object of this invention is to provide a light conducting mirror/fiber optic probe apparatus for examination and illumination of dental surgical and extraction sites having limited visibility.

BRIEF DESCRIPTION OF THE DRAWINGS

Further objects and advantages of the invention will appear from the following description as well as from the accompanying drawings which illustrate certain embodiments of the invention. It will be understood that the invention is not limited to the embodiments described and that the drawings are for purposes of illustration only and are not intended as a definition of the limits of the invention. Similar reference characters denote similar elements throughout the several views.

FIG. 1. is a side elevation view of a light wand shining light through an embodiment of the light conducting dental apparatus of this invention;

FIG. 2 is a fragmentary, longitudinal sectional view of a second embodiment of a light conducting apparatus constructed in accordance with the present invention;

FIG. 3 is a perspective view of a portion of an embodiment of the light conducting apparatus of this invention, being utilized to place dental restorative material in a cavity preparation in accordance with the present invention;

FIG. 12 is a front elevation view of a portion of a combination mirror and oral illuminator constructed in accordance with the present invention, with the mirror supporting rod shown in phantom;

FIG. 13 is a side elevation view of a portion of the combination mirror and oral illuminator of FIG. 12, constructed in accordance with this invention;

FIGS. 14 through 23 are cross-sectional views of various configurations of the working end of an embodiment of the light conducting apparatus of this invention, wherein:

FIG. 14 is a cross-sectional view of a working end of an embodiment of the light conducting apparatus of this invention having a round configuration;

FIG. 15 is a cross-sectional view of a working end of an embodiment of the light conducting apparatus of this invention having a square configuration;

FIG. 16 is a cross-sectional view of a working end of an embodiment of the light conducting apparatus of this invention having a semi-circular configuration;

FIG. 17 is a cross-sectional view of a working end of an embodiment of the light conducting apparatus of this invention having an elliptical configuration;

FIG. 18 is a cross-sectional view of a working end of an embodiment of the light conducting apparatus of this invention having an inverted pyramid configuration;

FIG. 19 is a cross-sectional view of a working end of an embodiment of the light conducting apparatus of this invention having a crescent configuration;

FIG. 20 is a cross-sectional view of a working end of an embodiment of the light conducting apparatus of this invention having a rounded hemispherical configuration;

FIG. 21 is a cross-sectional view of a working end of an embodiment of the light conducting apparatus of this invention having a mono-beveled configuration;

FIG. 22 is a cross-sectional view of a working end of an embodiment of the light conducting apparatus of this invention having a bi-beveled configuration;

FIG. 23 is a cross-sectional view of a working end of an embodiment of the light conducting apparatus of this invention having a curved configuration;

FIG. 24 is a fragmentary, longitudinal sectional view of light source means in accordance with this invention;

FIG. 25 is a perspective, longitudinal sectional view of a portion of a combination mirror and fiber optic probe constructed in accordance with this invention;

FIG. 26 is a schematic, perspective view of an extrusion device constructed in accordance with this invention;

FIG. 27 is a longitudinal, sectional view of a portion of a light conducting apparatus for applying composite or bonding agent to a tooth in accordance with this invention.

DETAILED DESCRIPTION OF PREFERRED EMBODIMENTS

Figure 4:
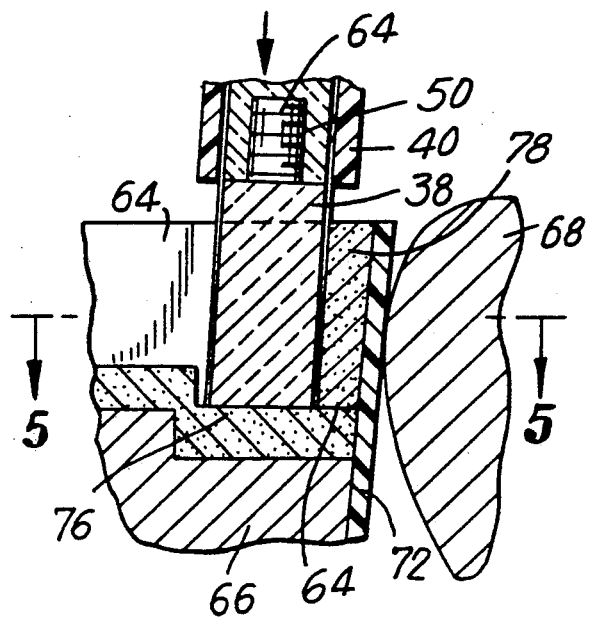
FIG. 4 is a cross-sectional view of a portion of the light conducting apparatus of FIG. 2 being utilized to place, compact, shape and polymerize dental restorative material in a cavity preparation in accordance with the present invention.

This invention relates, generally to a method and an apparatus for placing, compacting and shaping a light activated resin restorative material against a hard biological tissue or surface and for polymerizing said restorative material against said biological tissue or surface to produce a restoration. In particular, this invention relates to a method and apparatus for placing, compacting and shaping a light activated dental restorative material in a cavity preparation, between adjacent teeth or against a pulpal wall and for polymerizing said restorative material in said preparation, between said teeth or against said wall to produce a restoration. Light activated dental restorative material is defined to include composite resin material, bonding agent and calcium hydroxide. A restoration is defined to include replacement of a missing tooth, portion of a tooth, or crown as well as the production of a calcium hydroxide liner, base, direct pulp cap, pulpotomy or indirect pulp cap procedure. Using the present method, a dentist may insure depth of cure of the restorative material, maximize illuminating efficiency of the curing light, and keep exposure time required for polymerization of the restorative material to a minimum. Pull-back of the restorative material is avoided and shrinking or marring of the restoration is eliminated or minimized to a great degree.

To this end, the dentist places, compacts and shapes dental restorative material in a cavity preparation, between adjacent teeth or against a pulpal wall with an instrument designed for that purpose. One illustrative instrument, which is shown in FIG. 1 and described in more detail below, comprises a disposable, polished, rigid, fiber optic handle member having an exposed matted working end of reduced diameter and an opposite butt end for receiving light. While holding the handle member, the dentist uses the working end to place, compact and shape a lightactivated dental restorative material in a cavity preparation, between adjacent teeth or against a pulpal wall. Holding the working end against the shaped and compacted restorative material to maintain the desired shape of the restoration, the dentist or an assistant approximates a source of curing light to the butt end of the handle member and activates the light source. Curing light is transmitted substantially undiffracted through the length of the polished handle member and diffuses out from tip and all sides of the matted working end to impinge upon the restorative material until the latter is polymerized and bonds to the tooth. As the instrument is left in place during curing, there is no pull-back of the restorative material caused when the instrument is removed, and thus no shrinking or marring of the restoration. Leakage at the margins of the restoration and recurrent decay under the restoration are also eliminated or greatly minimized.

Referring now to FIG. 1 there is shown a light conducting apparatus 2 comprising an elongated, rigid handle member 4 having a working end 6 and an opposite butt end 8. The apparatus 2 is made of a fiber optic material; the handle member 4 has a polished cylindrical outer surface whereas the working end 6 has a matted or abraded outer surface.

In use, a source of curing light, usually a light wand 10, is approximated to the butt end 8 of the instrument. As noted previously, due in part to the surface characteristics of the apparatus curing light is transmitted substantially undiffracted along the length of the polished handle member 4 between its opposite ends and is emitted from the tip 12 and all sides of the matted working end 6 of the apparatus 2.

The working end 6 of the apparatus 2 is adapted to place, compact, and shape light activated dental restorative material in a cavity preparation, between adjacent teeth or against a pulpal wall to polymerize said material in said preparation, between said teeth or against said wall. It is preferred that the working end 6 of the handle member 4 have a reduced diameter as compared to the handle member 4 to facilitate insertion into the preparation, tooth or pulpal wall.

The handle member 4 may have a straight, elongated rod configuration or may optionally have a bent, elongated rod configuration as illustrated in FIG. 1. It is contemplated that the working end 6 of the handle member 4 may also be straight or angled relative to the handle member 4 for increased access to the tooth under treatment. The configuration of the working end 6 of the apparatus 2 is advantageously selected for maximum access to the cavity preparation or tooth surface. It is envisioned that the working end 6 may have a bi-angled configuration to facilitate access to Class V lesions and buccal or lingual pits; the working end 6 may optionally be angled for back action, to facilitate access to class III lesions and lingual or anterior teeth.

It is further envisioned that a selection of such instruments, having working ends 6 in various shapes, sizes and crosssectional configurations be available for selection by the dentist. Among the shapes and cross-sectional configurations envisioned for the working end 6 of the apparatus 2 of FIG. 1. and illustrated in FIGS. 14 through 24 are: round, square, semicircular, elliptical, inverted pyramid shaped, crescent, curved hemisphere, and mono- and bi-beveled configurations. Other configurations not shown include conical, spatula, cylindrical, domed, oblong, oval, planar, square, tapered, spherical and triangular. It will be understood that the configurations contemplated are not limited to those enumerated or illustrated.

Dentists typically must place and polymerize dental restorative material in hard to reach or unusually shaped cavity preparations or other surfaces. It is accordingly a feature of this invention that the working end 6 of the apparatus 2 may be shaped or milled by the dentist chairside to conform to a desired configuration approximating that of a cavity preparation or a tooth to be restored. Such shaping is accomplished simply by heating the instrument until it is softened and then bending and/or carving the working end to the desired shape, size and cross-sectional configuration. Alternatively, the working end of the instrument may be cut with a handpiece or other instrument to the desired configuration. The working end is then sanded to achieve a matte surface.

It is apparent that such shaping may also be accomplished automatically rather than manually by means of an extrusion-molding device such as is schematically illustrated in FIG. 26. An insulated metal box 14 having a face place 16, bottom 18 and side walls 20 is provided. Depicted on the face plate 16 are a number of apertures 22 in a variety of shapes and sizes; slots 24 corresponding to the shape, size and cross-sectional configuration of the apertures 22 are provided in the device, as shown in phantom lines in FIG. 26. The box 14 is equipped with a transformer 26 which connects to an electrical outlet. A heating coil 28 activated by a switch heats the box. The dentist determines the shape which is most appropriate for the particular restoration or other task and inserts the working end 6 of the apparatus 2 into the aperture 22 and slot 24 having the desired shape. The working end 6 is heat milled or extruded into the desired configuration, leaving no ledges, fissures or undercuts. The working end is then sanded to regain its matted finish.

In accordance with this invention, the apparatus 2 is preferably made from a transparent, light conductive material which is dimensionally stable and chemically inert, so that no bonding occurs between the instrument and the composite or the tooth; is resistant to most organic solvents, has a lot specific gravity and adequate tensile strength; is abrasion resistant, tasteless and odorless; is injection moldable and has a low softening temperature, so that it may be easily shaped chairside; and is optionally radio-opaque so as to be visible on an X-ray. Materials which possess these properties and which are preferred for the instrument of this invention include methylmettacrylate, ethylmethacrylate, methacrylic acid polymer, and polycarbonate. It is envisioned that the apparatus be available in a sealed package to assure sterility, and is disposable or sterilizable.

Referring now to FIG. 2, a second embodiment of a light conducting apparatus in accordance with this invention is shown for placing, compacting and shaping a light activated dental restorative material in a cavity preparation, between adjacent teeth or against a pulpal wall, and for polymerizing said material in said preparation or between said teeth by exposing the material to curing light from the tip and all sides of the working end member of the apparatus. The apparatus may be used in combination with a hand held light wand 10 which is connected to a light source, not shown.

The apparatus 36 comprises a rigid, rod shaped handle member 40 having a proximal end 42 and an opposite distal butt end 44. The proximal end 42 of the handle member 40 is connected to a working end member 38 of the apparatus 36 and the distal butt end 44 of the handle member 40 is connected to a source of curing light. The handle member 40 comprises a fiber optic core 46 enclosed on its side surfaces, between its ends 42 and 44, within an opaque coating or housing 48 which prevents light, transmitted from end to end thereof, from being substantially visible from the side surfaces of the handle member 40. A threaded longitudinal recess 50 is disposed in the proximal end 42 of said handle member 40.

The proximal end 42 of the handle member 40 of the apparatus 36 is connected to a removable and replaceable fiber optic working end member 38, which is preferably matted. The working end member 38 is configured so as to optimally place, compact and shape a light activated dental restorative material in or on a tooth or between teeth. The working end member 38 is held against the shaped and compacted restorative material to maintain the desired shape of the restoration while the restorative material is exposed to curing light emitted from the tip and sides of the working end member 38. The dental restorative material in thus polymerized and bonded to the tooth and pull-back, shrinking and marring problems are avoided or minimized.

In accordance with this invention, the fiber optic core 46 of the handle member 40 is made from a light conductive material, such as described above. The opaque housing 48 of the handle member 40 may be metal or plastic. The opaque floating or housing 48 on the side surfaces of the handle member 40 substantially prevents curing light from irritating the dentist's eyes while polymerizing restorative materials.

The working end member 38 shown in FIGS. 2 and 4 has a cylindrical configuration with a square tip. It will be understood that the sides and tip of the working end member 38 may be round or a variety of other shapes as described in more detail below. The objective is to have the working end member configured so as to quickly and easily apply a light activated dental restorative material in or on a tooth or between adjacent teeth. The working end member may optionally be shaped to conform to a desired configuration approximating that of a surface or surfaces of a cavity preparation or a tooth to be restored.

The distal butt end 44 of the handle member 40 is connected to a source of curing light by means of an opaque, substantially conical adaptor 52 adapted to engage and retain the end of a composite light wand 10 of variable dimensions. It is contemplated that the dentist hold the light conducting apparatus 36 and an assistant hold the light wand 10.

The adaptor 52 has a distal end 54 defining a generally circular enlarged opening for engaging and retaining light-wand 10 and a proximal end 56 defining a reduced opening. A tubular sleeve 58 is formed integrally with and projects axially from the reduced proximal end 56 of the adaptor 52. The sleeve 58 is adapted to receive and frictionally and removably engage with the distal butt end 44 of the handle member 40 of the apparatus 36. The adaptor 52 preferably has a light reflective interior surface 59 and operates to concentrate the light in addition to holding the light wand 10 in a spaced relation to the apparatus 36 of the invention.

There is some deformation of the adaptor sleeve 58 and the distal butt end 44 of the handle member 40 so as to permit sufficient frictional engagement between the adaptor 52 and the handle member 40. To facilitate locking engagement of the adaptor sleeve 58 and the handle member 40, a rib 60 or other projection may be provided on the external surface of the distal end 44 of the handle member 40 for engagement with a complementary opening 62 in the adaptor sleeve 58. The diameter of the rib 60 is preferably greater than the width of the opening 62 so that a snap action results when the rib 60 engages with or is released from the opening 62 in the sleeve 58. The adaptor 52 is locked onto the handle member 40 when the rib 60 on the handle member 40 is pressed through and engages with the opening 62 in the adaptor sleeve 58. The adaptor 52 is released when the rib 60 on the handle member 40 and the opening 62 in the sleeve 58 are pulled apart from each other. Any number of such ribs or projections may be provided; in the preferred embodiment one circumferential rib 60 is provided on the distal end 44 of the handle member 40 engageable with a corresponding opening 62 in the adaptor sleeve 58. The adaptor 52 can thus easily be manually removed and replaced.

As will be explained, the working end member 38 is independently removably attached to the proximal end 42 of the handle member 40, so as to permit the dentist to selectively remove and replace the working end member with another member having a different shape, size or cross sectional configuration with minimum interruption of his work. It is envisioned that a supply of interchangeable working end members in a variety of shapes, sizes and cross-sectional configurations for convenient application of dental restorative material in or on a tooth, or between adjacent teeth will be available for selection by the dentist. The dentist selects the working end member having the configuration required to assure optimal contact of the restorative material with the margin and internal aspects of the cavity preparation or other tooth surface.

Any means for rapid interchange of the working end member 38 by mounting onto and removal from the handle member 40 is acceptable. In a preferred embodiment the working end member 38 is threadably mounted on the proximal end 42 of the handle member 40 for quick attachment and detachment from the handle member 40. As illustrated in FIG. 2, a threaded cylindrical rod 64 disposed longitudinally in the rearward end of the working end member 38 threadably engages the threaded longitudinal recess 50 disposed in the proximal end 42 of the handle member 40 and thereby detachably mounts the working end member 38 on the proximal end 42 of the handle member 40.

For use, the dentist activates the light source, not shown, which transmits light to the hand-held light wand through a fiber optic cable, not shown. Light is transmitted through the handle member 40 of the apparatus 36 and is emitted from the tip and sides of the working end member 38 for a sufficient& length of time to polymerize the dental restorative material 30.

The following section deals with the operation of the light conducting apparatus of this invention. Referring now to FIG. 3 the apparatus of FIG. 1 is shown applying dental restorative material to a class II cavity preparation. It will be understood that the following description is equally applicable to the embodiment of the apparatus shown in FIG. 2 and later figures and that the invention may be used in conjunction with light activated dental restorative materials in areas that are not easily accessible.

A modified Class II cavity preparation 64 in the first pre-molar tooth 66 adjacent the canine 68 and second premolar 70 teeth is shown in FIG. 3. The cavity preparation 64 has a boxlike design, with slightly converging (toward the occlusal) walls, a basically flat floor and undercuts in dentin for retention. A bevel on the occlusal cavosurface margin of the class II cavity preparation, with a width of approximately 0.5 mm at an angle of approximately 45 degrees to the external enamel surface, is preferred as it provides more surface area for bonding and potentially strengthens the remaining tooth structure.

A mylar matrix strip 72 is inserted around the tooth having the cavity. A wedge 74 is placed in the gingival proximal region to separate the canine 68 and premolar 66 teeth to assure proper contour and proximal contact of the finished restoration after removal of the matrix strip 72. The tooth 66 is acid etched so as to produce microundercuts in the enamel. The dental restorative material is then placed in two stages. First, a thin bonding agent is applied which engages the microundercuts in the enamel to provide mechanical retention. The dental restorative material is then added and chemically bonds with the bonding agent, forming a strong attachment between the tooth and the restoration. In FIG. 3, the working end 6 of the apparatus 2 is shown carrying dental restorative material 30 prior to insertion into the cavity preparation 64.

Referring generally to FIGS. 2, 3 and 4, a small amount of the dental restorative material 30 is picked up on the working end member 38 of the apparatus 36, inserted into the cavity preparation 64 and pressed or closely adapted by the working end member 38 of the apparatus 36 onto the walls or other etched surface of the preparation to prevent microleakage. The dental restorative material 30 may be manipulated, compacted and shaped by the working end 38 of the apparatus 36 before polymerization. While the working end member 38 is held against the shaped and compacted restorative material 30 to maintain the desired shape of the restoration, the light source is activated so that the restorative material 30 is exposed to curing light transmitted through the handle member 40 and emitted from the tip and sides of the working end member 38 for 20 seconds or more. The restorative material is thus polymerized and bonds to the tooth. This procedure is followed for each wall and each line angle of the cavity preparation.

If the restoration is under-contoured, more restorative material 30 can be added over the first increment and cured. With large restorations and deep cavity preparations with retentive undercuts it is preferred to add and polymerize the restorative material in many increments to minimize the effects of polymerization shrinkage and ensure complete polymerization in remote areas.

Figure 6:
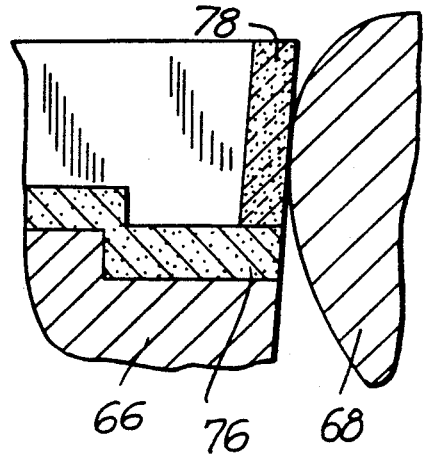
FIG. 6 is a cross-sectional view of the restored cavity preparation.
Figure 5:
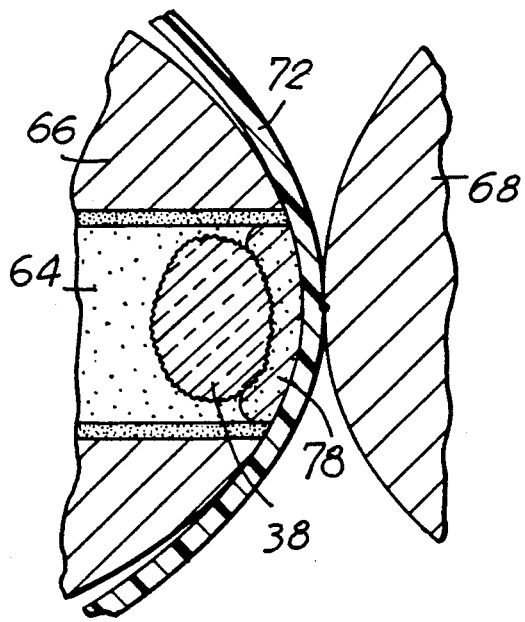
FIG. 5 is a cross-sectional top view taken along lines 5—5 of FIG. 4.

Referring now to FIGS. 4 through 6, the light conducting apparatus is shown placing, compacting and shaping a second increment of dental restorative material in a cavity preparation to restore contact between the first premolar and canine teeth. In FIG. 4, a small amount of restorative material 30 inserted on the working end member 38 is placed, compacted and shaped on the floor of the cavity preparation 64 and polymerized while the working end member 38 is held against the shaped and compacted restorative material in the preparation 64. This first increment of restorative material 30 is indicated by numeral 76 and is generally placed on the floor and either side of the cavity preparation. The mylar matrix 72 is displaced towards the adjacent tooth by the restorative material. A second increment 78 of restorative material is then placed by the working end member 38 against the mylar to restore tight contact between the first premolar and the canine teeth. The second increment 78 is compacted and shaped as close to the final contour as possible using a working end member having a substantially circular crosssection, as shown in FIG. 5. Curing light is transmitted through the length of the handle member 40 and is emitted from the tip and sides of the working end member 38 so as to polymerize the second increment 78 of the restorative material 30. As the working end member 38 of the apparatus 36 is held in place against the shaped and compacted restorative material 30 in the preparation 64 while the restorative material 30 is polymerized, no pull-back or shrinking problems occur and the surface of the restoration is as close to active contact with the adjacent tooth as possible. Illustrated in FIG. 6 is the restored emergence profile of the teeth (66 and 68) after the wedge 74 and mylar matrix 72 are removed and contact between adjacent teeth is restored. The restoration is then built up to contour and finished using a handpiece and finishing burs.

Figure 7:
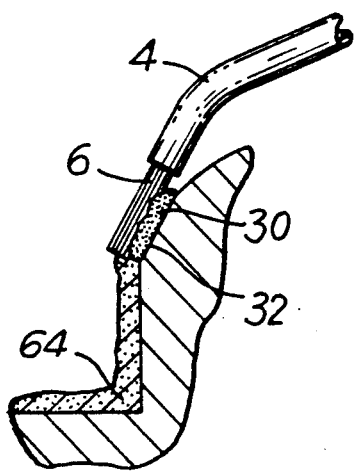
FIG. 7 is a cross-sectional view of a portion of an embodiment of the light conducting apparatus of this invention, being utilized to place, compact and shape dental restorative material to a cavosurface bevel of a cavity preparation in accordance with the present invention.

Referring now to FIG. 7, the working end 6 of the handle member 4 of the apparatus 2 of FIG. 1 is shown placing, compacting and shaping dental restorative material 30 to a cavosurface bevel 32 of a cavity preparation 64. The working end 6 of the apparatus 2 is advantageously configured to conform to the configuration of the bevel 32 to insure depth of cure and to prevent microleakage. It will be understood that the above description is equally applicable to the working end member 38 of the apparatus of FIG. 2.

Figure 8:
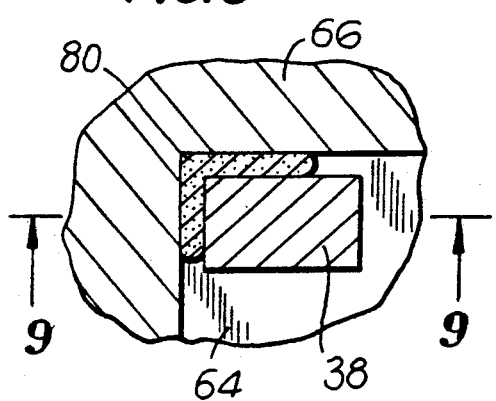
FIG. 8 is a cross-sectional top view of an embodiment of the light conducting apparatus of this invention being utilized to place, compact, shape and polymerize dental restorative material to a point angle of a cavity preparation, in accordance with the present invention.
Figure 9:
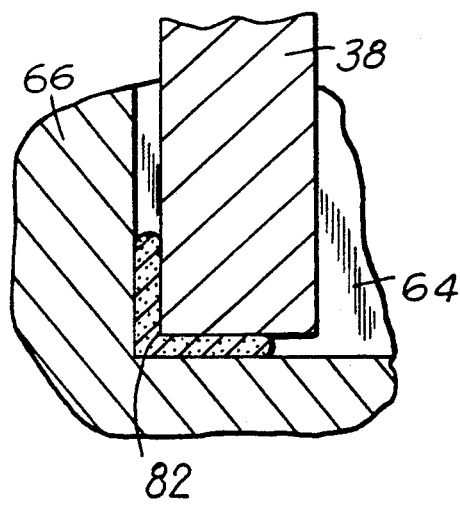
FIG. 9 is a cross-sectional top view taken along lines 9—9 of FIG. 8.

As disclosed, a supply of working end members in a variety of shapes, sizes and cross-sectional configurations will be available for selection by the dentist to assure optimal contact of the restoration with the margin and internal aspects of the cavity preparation. Referring now to FIGS. 8 and 9, rectangular configurations of the working end member 38 of the apparatus are shown which allow the dentist to adapt the dental restorative material to conform exactly with the point angle 80 (FIG. 8, top view) or line angle 82 (FIG. 9, side view) formed by the juncture of two walls of the cavity preparation 64.

The apparatus of this invention may also be used to apply a light activated calcium hydroxide liner or base to the pulpal wall of a tooth. Typically, if caries removal exceeds approximately 0.5 mm or less proximity to the pulp, a light activated calcium hydroxide liner or base is placed against the pulpal wall for pulpal protection and to stimulate dentin formation from inside the pulp. The working end of the apparatus may be used to apply and manipulate the light activated calcium hydroxide liner or base to the pulpal wall of a tooth. The working end of the apparatus is held against the shaped and compacted light activated calcium hydroxide to maintain the desired shape while the liner or base is polymerized by exposure to curing light emitted from the tip and sides of the working end of the apparatus.

Figure 10:
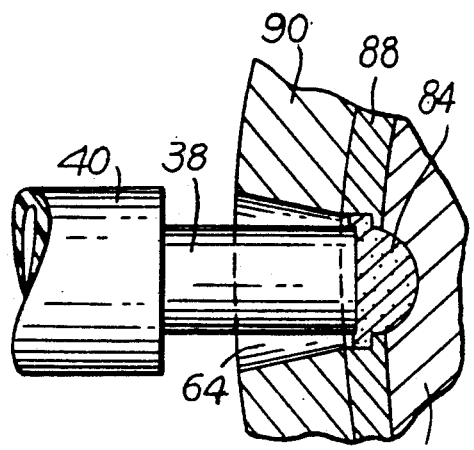
FIG. 10 is a cross-sectional view of a portion of an embodiment of the light conducting apparatus of this invention, being utilized to place, compact, shape and polymerize calcium hydroxide to the dentin portion of a tooth to seal off the pulp in accordance with the present invention.

In the event of a small exposure to the nerve or to the pulp of the tooth, a direct pulp cap procedure or pulpotomy may be followed to seal off the pulp, using the apparatus of this invention. Referring to FIG. 10, the dental pulp 86, dentin 88 and enamel 90 portions of the tooth are illustrated. The working end member 38 of the apparatus 36 is used to place a small amount of light curable calcium hydroxide 84 over the exposure in the dental pulp 86 and to hold the shaped and compacted restorative material in place while the calcium hydroxide is polymerized by exposure to a curing light transmitted as described above. Obviously, best results are achieved using a working end member 38 having a diameter greater than the diameter of the exposure to ensure a complete seal of the exposure, thereby prevent infection of the pulp.

Figure 11:
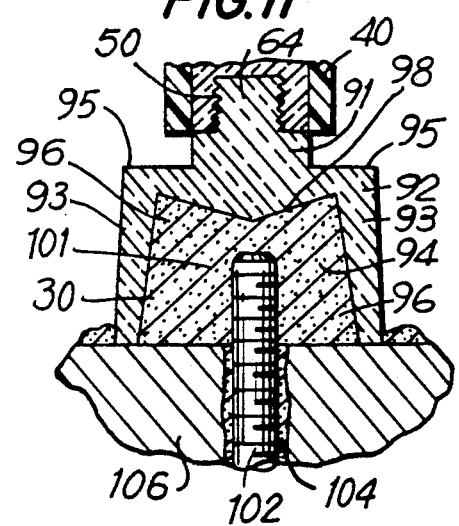
FIG. 11 is a fragmentary, longitudinal sectional view of an embodiment of the working end of the apparatus of this invention being utilized for core buildup in a post and core restoration.

In a further embodiment of this invention, the apparatus 36 may be used for placing, compacting, shaping and polymerizing dental restorative material 30 for core build-up in a host and core restoration of a tooth, for acceptance of a cast crown restoration. In this embodiment, the working end member has a configuration corresponding to the ideal crown preparation of the particular tooth to be restored. It is contemplated that a variety of working end members in a variety of sizes and contours, corresponding to the ideal crown preparation for a tooth to be restored, will be available for core build-up of that tooth. For illustrative purposes, shown in FIG. 11 is a working end member 38 of the apparatus adapted to place, compact and shape dental restorative material for core build-up of a post and core restoration of a molar or premolar. The working end member shown in FIG. 11 comprises a first fiber optic section 91 engageable with the handle member 40 of the apparatus 36 and a second section comprising a substantially cylindrical housing member 92 having exterior top walls 95, exterior side walls 93 and an interior chamber 94 defining a crown former for holding a fixed amount of light activated dental restorative material 30. The chamber has a generally M-shaped cross-section, is comprised of interior side 96 and interior top 98 walls and is open at its bottom end 100. The interior side walls 96 of the M-shaped chamber are tapered generally upwardly and inwardly from the exterior walls 93 at a six degree angle; the interior top walls of the chamber are preferably tapered downwardly and inwardly to simulate the cusps. The crown-former working end member is referred to generally by numeral 101. It will be understood that the second section of the working end member may have the configuration of the ideal crown preparation of any tooth to be restored.

In a post and core restoration, after a root canal is completed, the preparation for the post is typically achieved by removal of guttapercha and preparation of the canal space. A post 102 is inserted and cemented into the canal space 104 extending several millimeters into the coronal area of the tooth 106. In use, the dentist mounts the crown-former working end member 101 on the handle member 40 of the apparatus 36 in the manner previously described, shapes the cervical or bottom edge of the instrument with scissors or a bur and fills the interior chamber of the housing member 92 with a light activated dental restorative material 30. The crown former working end member 101 is cen- trally positioned over the post 102 and sealed to the cavosurface margin of the tooth. The restorative material 30 surrounds the post which projects up into the interior chamber 96 of the housing member 92 of the crown former working end member 101. The crown former working end member 101 builds up the post to the ideal dimensions of the crown preparation for that particular size and number tooth. The dental restorative material 30 is cured, bonding to the post 102 and adhering to the shoulder of the tooth in the manner described previously. The crown former working end member 101 is removed and the crown preparation is then reduced or adapted for acceptance of a cast crown restoration.

In the preferred embodiment, the first section 91 of the crown former working end member 101 is mounted on the handle member of the apparatus in substantially the same manner described above, i.e., a threaded cylindrical rod 64 is disposed longitudinally in the rearward end of the first section 91 of the crown former working end member 110 and threadably engages the threaded longitudinal recess 50 disposed in the proximal end 42 of the handle member 40, thereby detachably mounting the crown former working end member 101 on the proximal end 42 of the handle member 40 of the apparatus 36.

In another embodiment of this invention, the apparatus 36 may be used for placing, compacting, shaping and polymerizing dental restorative material 30 for complete coronal build-up of a tooth to be restored. In this embodiment, the working end member of the apparatus would have the configuration of the ideal tooth morphology for the particular tooth to be restored. It is contemplated that a variety of working end members in a variety of sizes and contours, corresponding to the ideal tooth morphology for a tooth to be restored, will be available for complete coronal build-up of the tooth. The working end member would be filled with composite, positioned over the tooth and cured in place in a manner substantially similar to that descried for the embodiment of FIG. 11. When cured, the coronal build-up will result in a final coronal restoration completely restoring the tooth to form and function. The working end member of the apparatus is removed from the tooth and the coronal restoration is finished by polishing with paste or burs.

The apparatus the apparatus 36 may also be used for placing, compacting, shaping and polymerizing dental restorative material 30 for partial coronal build-up of a tooth to be restored, i.e. for build-up of cusps, or for inlays or onlays. In this embodiment, the working end member of the apparatus is the same as that used for complete coronal build-up of the tooth to be restored, i.e. The working end member has a configuration corresponding to the ideal tooth morphology for the particular tooth to be restored. However, for partial coronal build-up, that portion of the working end member which is not needed is cut away or removed. The working end member is used to place, compact and shape restorative material on the tooth in the manner previously described and to polymerize the material so as to produce a partial coronal restoration.

In a further embodiment of this invention, the working end member may be used to apply light curable dental impression material on a tooth. In this embodiment, the working end member would have a substantially cylindrical shape with one end open to receive and retain impression material. In use, the open end of the cylindrical member is filled with impression material and seated on the tooth to take an impression of the tooth. A variety of members in different sizes may be provided for optimum fit; alternatively, the cylindrical member may be flamed, crimped and cut to size.

A further embodiment of the working end member 38 of the apparatus 36 is disclosed in FIG. 27. In this embodiment, the working end member comprises first fiber optic section 107 engageable with the handle member 40 of the apparatus 36 and a second section fixedly connected to the first section, the second section comprising a fiber optic brush 108 having clear plastic bristles. The bristles are preferably made of nylon or other similar material which is flexible and non-retentive to the surface to be restored. As described in previous sections, dental restorative material is defined to include bonding agent, which is applied or painted onto the etched area of a tooth or cavity preparation and engages the microundercuts in the enamel to provide mechanical retention. Dental restorative material in the form of composite resin is then placed, compacted and shaped and chemically bonds with the bonding agent upon polymerization. The brush working end member 110 is adapted to apply a thin coat of light activated bonding agent onto a tooth or cavity preparation. This is especially useful when applying liquid bonding agent to the external surface of the preparation or surface to be restored since the brush acts as a support for the material during placement, preventing pooling and uneven distribution of the liquid. The bonding agent is distributed evenly or thinned with a gentle stream of air and cured in the manner described earlier.

Alternatively, the brush working end member 110 may be used to apply composite material to the preparation or tooth to be restored. Using a brush is advantageous in build-up of the preparation and in the placement of composite on such surfaces as the incisal edge of an anterior tooth, as the bristles retain the material and prevent "creep" of the composite material prior to curing.

The first section 107 of the brush working end member 110 is mounted on the handle member of the apparatus in substantially the same manner described above, i.e. a threaded cylindrical rod 64 is disposed longitudinally in the rearward end of the first section 107 of the brush working end member 110 and threadably engages the threaded longitudinal recess 50 disposed in the proximal end 42 of the handle member 40, thereby detachably mounting the brush working end member 110 on the proximal end 42 of the handle member 40 of the apparatus.

As described above, the handle member of the apparatus of FIG. 2 accommodates an assortment of interchangeable working end members. In a further embodiment of this invention, a compact, easily manipulated combination mirror and oral illuminator independently removably attachable to the handle member of the light conducting apparatus of FIG. 2 is disclosed as the working end member.

Referring now to FIGS. 12 and 13, the combination mirror/ oral illuminator 112 comprises a substantially circular mirror 114 having a front reflective surface 116 and a back supporting surface 118. A fiber optic ring 120 is secured to and circumferentially bounds the perimeter of the mirror 114. A metal or plastic supporting rod 122, shown in phantom in FIG. 12, connects the back surface 118 of the mirror 114 to a hollow collar member 124 which is adapted to slide over and frictionally engage with the proximal end 42 of the handle member 40 of the apparatus 36 so as to mount the mirror/oral illuminator 112 on the handle member 40.

Light is conducted from a light source via the handle member 4 to the fiber optic ring to illuminate the mirror. This is accomplished by means of a fiber optic member 126 having one end integrally connected with the fiber optic ring 120 and an opposite threaded end 128 fixedly disposed in the collar 124 for threadably engaging with the recess 50 in the proximal end 42 of the handle member 40.

To facilitate locking engagement of the collar 124 and the handle member 40, a rib 60 or other projection is provided on the external surface of the distal end 44 of the handle member 40 for engagement with a complementary opening 62 in the collar 124, in the manner described above.

Illumination for the mirror/oral illuminator 112 embodiment of the apparatus of this invention may be provided, not only by means of a light wand 10 connected to a light source and transmitted to the handle member via an adaptor 52, as described above and as shown in FIG. 2, but may also be provided by means of a portable light source.

The sectional view of FIG. 24 illustrates the tasic internal components of a portable light source 130 for use with this invention. The components are all mounted in a housing 132 which is removably attached to the handle member 40 of the apparatus 36. A bulb 134 is securely mounted and contained within the housing 132. A battery 136 in the housing 132 is the power source for the bulb 134; switch means 138 energize the batterybulb circuit to produce illumination. Light is conducted from the bulb 134 to the handle member 42 by a fiber optic member 140 having one end preferably in contact with the bulb 134 and an opposite end 143 threadably engaged with a threaded recess 142 disposed in the distal end 44 of the fiber optic core 46 of the handle member 40. It should be apparent that variety of bulbs and batteries are acceptable so long the proper degree of illumination is provided. The battery 136 shown in FIG. 24 is of the type commonly used in hearing aids, obviously a convenient arrangement for a portable system; the battery 136 may be replaced via access panel 144 in housing 132, shown in the open position in phantom lines in FIG. 24. Upon closing of the switch from OFF to ON condition, which in series connects the battery 136 to the bulb 134, the bulb 134 is turned ON to provide illumination.

It will be understood that a portable light means such as is disclosed in FIG. 24 and described above may also be used to provide illumination for other embodiments of the apparatus of this invention. In a preferred embodiment, portable light means 130 may be used to provide bleaching light for bleaching teeth with superoxol ®. In this embodiment, the working end member 38 of the apparatus 36 is used to apply superoxol ® a tooth bleaching compound, on a tooth in the manner previously described. Portable light means substantially as described, mounted on the handle member provides bleaching light which is transmitted by the handle member 40 and emitted from the tip and sides of the working end member 38 as disclosed; superoxol ® is heated by the bleaching light emitted from the working end member and permeates the enamel rods and dentinal tubules of the tooth, bleaching the tooth.

In a further embodiment of this invention, a combination mirror and fiber optic probe is disclosed for examination of dental areas having limited visibility. The mirror and fiber optic probe combination 146 illustrated in FIG. 25 is independently removably attachable to the handle member 40 of the light conducting apparatus 36 of FIG. 2 and is interchangeable with the working end members 38 previously described.

Referring now to FIG. 25, the combination mirror and fiber optic probe 146 comprises a mirror 148 for intra-oral use, a fiber optic probe 150 and a collar 152 for slidably and removably receiving and frictionally engaging with the proximal end 42 of the handle member 40 of the apparatus 36. The mirror 148 is connected to the collar 152 by means of a connecting rod 154 having one end fixedly mounted on the mirror 148 and the other end fixedly mounted on the collar 152.

The fiber optic probe 150 comprises an elongated, flexible, fiber optic filament 156 having a first mounting part 158 disposed within the collar 152 for removably engaging with the proximal end 42 of the fiber optic core 46 of the handle member 40 and a third probing part 160 for illuminating and probing dental areas of limited visibility. The first 158 and third 160 parts of the fiber optic filament 156 are integrally connected by a second part 162 external to the collar 152. This second part 162 is enclosed within a tubular, flexible, opaque sheath 164. The sheath has one end fixedly mounted on the collar 152 and an opposite end adjacent to and substantially coaxial with the third part 160 of the fiber optic filament 150. The sheath prevents light transmitted from end to end of the fiber optic filament 150 from being substantially visible from the side surfaces of the filament 150. Light is emitted only from the third probing part 160 of the filament.

The fiber optic probe 150 is useful in accessing, probing and illuminating any small biological cavity. Specifically, in dental applications, the probe may be inserted into such cavities as extraction sites, endodontic canals, and sinuses for probing and proximally illuminating these cavities. The probe also has utility in oral surgery, for instance in probing and illuminating the site of an apicoectomy.

The probe 150 may be made of silicone or any other flexible, transparent, threadable, filamentous material and is replaceable within the sheath 164. The sheath may comprise a segmented or goose-necked opaque metal or plastic structure, as indicated in FIG. 25. The objective is that the sheath the flexible and easily manipulated.

In the preferred embodiment, the first mounting part 158 of the fiber optic filament 156 removably engages with the proximal end 42 of the fiber optic core 46 of the handle member 40 by means of a threading engagement substantially as described previously. That is, the first mounting part 158 of the fiber optic filament 156 has a threaded end for threadably engaging with the recess 50 in the proximal end 42 of the handle member 40.

The collar 152 of the combination mirror and fiber optic probe is slightly compressible so as to permit sufficient frictional engagement between the collar 152 and the handle member 40. To facilitate locking engagement of the collar 152 and the handle member 40, a rib or other projection 60 is provided on the external surface of the distal end 44 of the handle member 40 for engagement with a complementary opening, not shown, in the collar 152.

The light source for the combination mirror/fiber optic probe embodiment of this apparatus may be a light wand 10 connected to a light source as described above and as shown in FIG. 2. Alternatively, a portable light source as described earlier and as shown in FIG. 24 may be used with this embodiment.

While a number of embodiments of the present invention have been shown and described, it will be obvious to one skilled the art that many changes and modifications may be made thereto without departing from the spirit and scope of the invention.

What is claimed is:

1. A method for placing, compacting and shaping a light activated dental restorative material in a cavity preparation, between adjacent teeth or against a pulpal wall and for polymerizing said material in said cavity preparation, between said teeth or against said wall to produce a restoration, comprising the steps:
   a. providing a disposable, polished, rigid, fiber optic handle member having an exposed matted working end of reduced diameter and an opposite butt end for receiving light,
   b. heating the working end of the handle member and shaping the tip and sides of said working end to a desired configuration approximating that of a surface or surfaces of the cavity preparation, tooth or pulpal wall to be restored,
   c. while holding the said handle member, using said working end to place, compact, and shape a light-activated dental restorative material in a cavity preparation or between adjacent teeth,
   d. while the working end is held against the shaped and compacted restorative material to maintain the desired shape of the restoration, approximating a source of curing light to the butt end of the said handle member and activating the light source, whereby curing light is transmitted substantially undiffracted through the length of said polished handle member and diffuses out from the tip and all sides of said matted working end to impinge upon said restorative material until the latter is polymerized.

2. The method of claim 1, wherein after step a. and before step b. heating and shaping the handle member to a desired configuration.

3. The method of claim 1, wherein steps c and d are repeated to place, compact, shape and polymerize a second potion of dental restorative material adherent to the earlier placed portion of restorative material.

4. A method for placing, compacting and shaping a light activated resin restorative material against a hard biological tissue or surface and for polymerizing said material against said tissue or surface to produce a restoration, comprising the steps:
   a. providing a disposable, polished, rigid, fiber optic handle member having an exposed matted working end of reduced diameter and an opposite butt end for receiving light,
   b. heating the working end of the handle member and shaping the tip and sides of said working end to a desired configuration approximating that of a surface of surfaces of the biological tissue or surface to be restored,
   c. while holding the said handle member, using said working end to place, compact, and shape a resin restorative material against a hard biological tissue or surface,
   d. while the working end is held against the shaped and compacted restorative material to maintain the desired shape of the restoration, approximating a source of curing light to the butt end of the said handle member and activating the light source, whereby curing light is transmitted substantially undiffracted through the length of said polished handle member and diffuses out from the tip and all sides of said matted working end to impinge upon said restorative material until the latter is polymerized.

5. The method of claim 4, wherein after step a. and before step b. heating and shaping the handle member to a desired configuration.

6. The method of claim 4, wherein steps c and d are repeated to place, compact, shape and polymerize a second portion of resin restorative material adherent to the earlier placed portion of restorative material.

7. The method of claim 4, wherein said hard biological tissue or surface is selected from the group consisting of tooth, enamel, dentin, bone, cartilage and connective tissue.

8. A light conducting apparatus for placing, compacting and shaping a light activated dental restorative material in a cavity preparation, between a adjacent teeth, or against a pulpal wall and for polymerizing said material in said preparation, between said teeth or against said wall, comprising:

a rigid handle member having a proximal and a distal end, said handle member comprising a fiber optic core enclosed on its side surfaces, between its ends, within an opaque housing which prevents light, transmitted from end to end thereof, from being substantially visible from the side surfaces of said handle member;

a removable and replaceable fiber optic working end member for placing, compacting and shaping a light activated dental restorative material in or on a tooth or between teeth, and for polymerizing said material in or on said tooth or between said teeth by exposing said material to curing light emitted from the tip and all sides of said working end member;

means for connecting the proximal end of said handle member with said working end member; and means for connecting the distal butt end of said handle member with a source of curing light, wherein the source of curing light is a hand-held light wand and wherein the means for connecting the distal butt end of said handle member with said curing light source comprises:

an opaque, substantially conical adaptor having a lightwand engageable distal end defining a generally circular enlarged opening and a proximal end defining a reduced opening, a tubular sleeve portion formed integrally with and projecting axially from the reduced proximal end thereof, said sleeve portion adapted to receive and frictionally and removably engage with the distal butt end of said handle member.

9. The apparatus of claim 8 wherein said adaptor has a lightreflective interior surface.

10. The apparatus of claim 8 further comprising a threaded longitudinal recess disposed in the proximal end of said handle member and a threaded cylindrical rod disposed longitudinally in the rearward end of said working end member for threadably engaging said recess in the proximal end of said handle member and thereby detachably mounting said working end member on the proximal end of said handle member.

11. The apparatus of claim 8, wherein the handle member has a straight, elongated rod configuration.

12. The apparatus of claim 8, wherein the handle member has a bent, elongated rod configuration.

13. The apparatus of claim 8, wherein said fiber optic material is selected from the group consisting of methacrylic acid polymer, methylmethacrylate, ethylmethacrylate or polycarbonate.

14. The apparatus of claim 8, wherein said working end member projects at an angle to said handle.

15. The apparatus of claim 8, wherein said working end member has a configuration approximating that of a surface or surfaces of a cavity preparation or tooth to be restored.

16. The apparatus of claim 8 wherein said working end member has a configuration corresponding to the ideal crown preparation for a tooth to be restored, said working end member adapted to place, compact and shape dental restorative material for core build-up in a post and core restoration and to polymerize said material in said tooth for acceptance of a cast crown restoration.

17. The apparatus of claim 8 wherein said working end member has a configuration corresponding to the ideal tooth morphology for a tooth to be restored, said working end member adapted to place, compact and shape dental restorative material for complete or partial coronal build-up of a tooth.

18. The apparatus of claim 8 wherein said working end member has a configuration corresponding to a surface or surfaces of the pulp of a tooth for sealing off the pulp in a direct pulp cap, pulpotomy or indirect pulp cap procedure.

19. A light conducting apparatus for placing, compacting and shaping a light activated dental restorative material in a cavity preparation, between adjacent teeth, or against a pulpal wall and for polymerization said material in said preparation, between said teeth or against said wall, comprising:

a rigid handle member having a proximal and a distal end, said handle member comprising a fiber optic core enclosed on its side surfaces, between its ends, within an opaque housing which prevents light, transmitted from end to end thereof, from being substantially visible from the side surfaces of said handle member;

a removable and replaceable fiber optic working end member for placing, compacting and shaping a light activated dental restorative material in or on a tooth or between teeth, and for polymerizing said material in or on said tooth or between said teeth by exposing said material to curing light emitted from the tip and all sides of said working end member;

means for connecting the proximal end of said handle member with said working end member; and means for connecting the distal butt end of said handle member with a source of curing light;

wherein said working end comprises a fiber optic brush having clear plastic bristles.

20. A light conductive apparatus for placing, compacting and shaping a light activated resin restorative material against a hard biological tissue or surface and for polymerizing said material against said biological tissue or surface, comprising:

a rigid handle member having a proximal and a distal end, said handle member comprising a fiber optic core enclosed on its side surfaces, between its ends, with an opaque housing which prevents light, transmitted from end to end thereof, from being substantially visible from the side surfaces of said handle member;

a removable and replaceable fiber optic working end member for placing, compacting and shaping a light activated resin restorative material against a hard biological tissue or surface and for polymerizing said material against said tissue or surface by exposing said material to curing light emitted from the tip and all sides of said working end member;

means for connecting the proximal end of said handle member with said working end member; and means for connecting the distal butt end of said handle member with a source of curing light, wherein the source of curing light is a hand-held light wand and wherein the means for connecting the distal butt end of said handle member with said curing light source comprises:

an opaque, substantially conical adaptor having a lightwand engageable distal end defining a generally circular enlarged opening and a proximal end defining a reduced opening, a tubular sleeve portion formed integrally with and projecting axially from the reduced proximal end thereof, said sleeve portion adapted to receive and frictionally and removably engage with the distal butt end of said handle member.

21. The apparatus of claim 20 wherein said adaptor has a light-reflective interior surface.

22. The apparatus of claim 20 further comprising a threaded longitudinal recess disposed in the proximal end of said handle member and a threaded cylindrical rod disposed longitudinally in the rearward end of said working end member for threadably engaging said recess in the proximal end of said handle member and thereby detachably mounting said working end member on the proximal end of said handle member.

23. The apparatus of claim 20, wherein the handle member has a straight, elongated rod configuration.

24. The apparatus of claim 20, wherein the handle member has a bent, elongated rod configuration.

25. The apparatus of claim 20, wherein said fiber optic material is selected from the group consisting of methacrylic acid polymer, methylmethacrylate, ethylmethacrylate or polycarbonate.

26. The apparatus of claim 20, wherein said working end member projects at an angle to said handle.

27. The apparatus of claim 20, wherein said hard biological tissue or surface is selected from the group consisting of tooth, enamel, dentin, bone, cartilage and connective tissue.

* * * * *